United States Patent [19]

D'Alelio, deceased

[11] Patent Number: 4,477,439

[45] Date of Patent: Oct. 16, 1984

[54] TREATMENT OF IRRITATED AND EXCORIATED AREAS AROUND THE STOMA OF OSTOMY PATIENTS

[75] Inventor: Gaetano F. D'Alelio, deceased, late of South Bend, Ind., by St. Joseph Bank & Trust Co., Executor

[73] Assignee: Walter J. Monacelli, St. Petersburg, Fla. ; a part interest

[21] Appl. No.: 253,602

[22] Filed: Apr. 13, 1981

[51] Int. Cl.$^3$ ............... A61K 33/04; A61K 33/06; A61K 33/30; A61K 33/42
[52] U.S. Cl. .................... 424/162; 424/128; 424/145; 424/154; 424/164
[58] Field of Search .............. 424/162, 164, 128, 4, 424/80, 78, 154

[56] References Cited

U.S. PATENT DOCUMENTS

| | | | |
|---|---|---|---|
| B 495,489 | 2/1976 | Chen | 424/4 |
| 3,804,949 | 4/1974 | Balassa | 424/128 |
| 3,814,797 | 6/1974 | Kasahara et al. | 424/128 |
| 4,083,965 | 4/1978 | Bluhm | 424/128 |
| 4,120,946 | 10/1978 | Queuille | 424/4 |

*Primary Examiner*—Frederick E. Waddell
*Attorney, Agent, or Firm*—Walter J. Monacelli

[57] ABSTRACT

The treatment described herein comprises the process of reducing the soreness of irritated or excoriated areas surrounding the stoma of ostomy patients by the application of a sulfate or phosphate of barium, calcium, strontium or zinc, preferably barium sulfate. This finely divided powder may be in the form of a dry powder, an aqueous suspension or paste, or an ointment or cream. This treatment brings relief in a short time and curing of the irritation, generally within 24 hours or more.

8 Claims, No Drawings

TREATMENT OF IRRITATED AND EXCORIATED AREAS AROUND THE STOMA OF OSTOMY PATIENTS

BACKGROUND OF THE INVENTION

1. Field of the Invention

This invention relates to a method for treatment of an irritated or excoriated area of the skin or flesh around the stoma of ostomy patients. More specifically, it relates to the application of a finely divided powder comprising a sulfate or phosphate of barium, calcium, strontium or zinc.

2. State of the Prior Art

Abdominal surgery for a number of illnesses involving different parts of the gastro-intestinal and urinary tract can result in the patient being left with an abdominal stoma or opening with a device for collecting the matter passing through the stoma. The most common types of abdominal stoma are the colostomy, the ileostomy and the ileal conduit. In many of these types of operations, the patient is unable to control the passage of bodily waste material and must rely upon the appliance attached to his or her body to collect this material.

These appliances are attached directly to the body by various means, such as an adhesive faceplate, mounting gasket, etc., which are fitted around the stoma. However, the nature of the fitting is such as to cause irritation or excoriation of the skin or flesh with which it comes in contact. This causes intense discomfort and pain to the patient. No satisfactory remedy has been found to avoid or quickly cure this problem.

SUMMARY OF THE INVENTION

In accordance with the present invention, it has been found that substantial relief and curative effect can be afforded to the irritated or excoriated skin or flesh around a stoma by the application of a finely divided powder of a sulfate or phosphate of an alkaline earth metal including barium, calcium, strontium and zinc. The preferred composition is barium sulfate. While this powder may be applied to the area as a dusting powder, the powder is easily brushed away and it is preferred to apply it as a paste, that is a suspension or colloid, or as an ointment or salve.

Regardless of the manner of application, it is advantageous to have the solid composition comprised predominantly of the specified powder, advantageously 90% or more, preferably 90-95% by weight. Various other materials may be present such as viscosity modifiers, dispersing agents, preservatives, anesthetics, etc., provided the added material does not cause further irritation. Generally it is desirable to have sufficient water present to make a paste that can be applied. Distilled or sterilized water is preferred.

Typical viscosity improvers or thickeners include methyl cellulose, polyvinyl alcohol, carboxymethyl cellulose, hydroxyethyl cellulose, povidone (polyvinyl-2-pyrrolidone), etc. Dispersing agents that may be used include dialkyl sodium sulfosuccinate, such as dioctyl sodium sulfosuccinate, dinonyl sodium sulfosuccinate, diheptyl sodium sulfosuccinate, dihexyl sodium sulfosuccinate, karaya gum, agar, bentonite, gelatin, silica gel, sodium carboxy methyl cellulose, hydroxypropyl methyl cellulose, methyl cellulose, tragacanth, etc.

Local anesthetics such as benzocaine (ethyl para-aminobenzoate), novociane, etc. may be used to alleviate pain. Suitable preservatives are methyl, ethyl and propyl paraben, preferably methyl paraben alone or mixed with ethyl or propyl paraben. These materials have the formula p—$HO-C_6H_4COOR$, wherein R is methyl, ethyl or propyl. These are also known as parasept and are known to retard molding in water solutions. Appropriate coloring agents and perfumes may also be added in minute amounts where desired.

The sulfate or phosphate salt should be at least of 95%, preferably 97.5% purity and free of grittiness. Typical salts are $BaSO_4$, $CaSO_4$, $Ca_3(PO_4)_2$, $Ba_3(PO_4)_2$, $Zn_3(PO_4)_2$, $SrSO_4$, $CaSO.2H_2O$, $CaF^3.3Ca_3P_2O_4$ (apotite), etc.

DETAILED DESCRIPTION OF THE INVENTION

While it is satisfactory to dust the sulfate or phosphate finely powdered salt on the irritated area, the powder becomes easily dislodged and therefore it is preferred that the powder be applied as a paste or cream. For such purpose, sufficient water or oily material such as mineral oil is added to the powder to give a satisfactory consistency as a paste or cream for application.

As indicated above, various modifiers are advantageously added to the salt, particularly when it is to be applied as a paste or cream. Such modifiers comprise 0.5-5% of a dispersing agent, 1-5% of a viscosity improving or thickening agent, 0.05-0.2% of a preservative, 0.5-2% of a local anesthetic, and possibly minute amounts of a coloring agent and a perfume. These percents are based on the total weight of the salt and the modifiers.

The following are typical, suitable compositions in which the $BaSO_4$ is a finely divided powder which passes through a 50 mesh screen (Tyler).

| Parts | Compound |
| --- | --- |
| A | |
| 94.8 | $BaSO_4$ |
| 2 | Methyl cellulose |
| 1 | Dioctyl sodium sulfosuccinate |
| 2 | Karaya gum |
| 0.2 | Methyl paraben |
| B | |
| 95 | $BaSO_4$ |
| 2 | Methyl cellulose |
| 0.8 | Dioctyl sodium sulfosuccinate |
| 2 | Karaya gum |
| 0.2 | Methyl paraben |
| C | |
| 94 | $BaSO_4$ |
| 2 | Methyl cellulose |
| 0.8 | Dioctyl sodium sulfosuccinate |
| 2 | Karaya gum |
| 0.2 | Methyl paraben |
| 1 | Benzocaine |

To these compositions there may be added diluent to form a paste or cream. The diluent may be water, an oil, such as mineral oil, or a more viscous or cream material such as vaseline. The oil and cream are advantageously of a type that can be tolerated by the skin so as not to cause further irritation. The amount of diluent is advantageously kept to a minimum to give a maximum concentration of the salt in contact with the skin. However, more dilute concentrations are also effective but require longer periods. With more dilute aqueous suspensions, several applications may be made with a waiting period in between applications so that the evaporation of the water would cause concentration of the salt.

Also as indicated above, the various modifiers in A, B and C may be replaced by other modifiers which will perform similar functions.

SPECIFIC EMBODIMENT

The invention is illustrated by the following examples which are intended merely for purpose of illustration and are not to be regarded as limiting the scope of the invention or the manner in which it may be practiced. Unless specifically indicated otherwise, parts and percentages are given by weight.

EXAMPLE I

The collection pouch of a colostomy patient is removed and the highly irritated excoriated skin area around the stoma is washed. A thin coat of very finely divided $BaSO_4$ powder dispersed in a small amount of water is applied in a thin layer over the irritated area. Then the powder is allowed to dry before the pouch connection is put back in place. Within 24 hours, the soreness is alleviated and the sores are completely healed in 4 days.

EXAMPLE II

A thick paste is made by adding just enough light mineral oil to a finely divided $BaSO_4$ powder. Application of this paste to the irritated, excoriated area around the stoma of a patient produces relief and curing of the sores within several days.

EXAMPLE III

The procedure of Example II is repeated using a mixture of 50 percent light mineral oil and 50 percent white vaseline, in place of the mineral oil, with similar successful results.

EXAMPLE IV

A thick paste is made by adding water to Composition A described above. This is applied to the exoriated stoma area of a colostomy patient and the pouch attached. The pain from the sores is almost all gone within 24 hours and the sores completely healed in 48 hours.

EXAMPLE V

The procedure of Example IV is repeated using Composition B described above. Similar results are obtained as in Example IV.

EXAMPLE VI

The procedure of Example IV is repeated using Composition C described above. Similar healing results are obtained as in Example IV but immediate relief from pain is effected by the benzocaine.

EXAMPLE VII

Relief is also obtained when Example VI is repeated using in place of the $BaSO_4$ similar weights respectively of very finely divided $CaSO_4$, $Ba_3(PO_4)_2$, $Zn_3(PO_4)_2$, $SrSO_4$, $Ca_3(PO_4)_2$ and $CaSO_2.2H_2O$ While certain features of this invention have been described in detail with respect to various embodiments thereof, it will be course be apparent that other modifications can be made within the spirit and scope of this invention, and it is not intended to limit the invention to the exact details insofar as they are defined in the following claims.

The invention claimed is:

1. A process for the external treatment of irritated areas of skin around the stoma of an ostomy patient comprising the external application of a finely divided alkaline earth metal salt selected from the class consisting of sulfates of barium, calcium, and strontium.

2. The process of claim 1, in which said finely divided salt is applied as a suspension in a liquid medium which is non-irritant to the skin.

3. The process of claim 1, in which said finely divided salt is applied as a paste of said salt suspended in water.

4. The process of any of claims 1, 2 or 3 in which said salt is barium sulfate.

5. The process of claim 4, in which said composition also contains a dispersing agent.

6. The process of claim 4, in which said composition also contains a thickening agent.

7. The process of claim 4, in which said composition also contains a preservative.

8. The process of claim 4, in which said composition also contains a local anesthetic.

* * * * *